United States Patent [19]
Ewen et al.

[11] Patent Number: 6,069,237
[45] Date of Patent: *May 30, 2000

[54] OPEN-PENTADIENYL METALLOCENEN LIGANDS, POLYMERIZATION CATALYSTS/ CATALYST PRECURSORS AND POLYMERS THEREFROM

[75] Inventors: John A. Ewen; Robert W. Strozier, both of Houston, Tex.

[73] Assignee: Montell Technology Company BV, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/526,376

[22] Filed: Sep. 11, 1995

[51] Int. Cl.[7] ................ C07F 5/00; C07F 9/00; C07F 17/00; C07F 7/00

[52] U.S. Cl. ............. 534/15; 502/102; 502/103; 502/117; 502/152; 502/155; 502/158; 556/11; 556/22; 556/23; 556/32; 556/43; 556/52; 556/53

[58] Field of Search .................. 534/15, 43, 52, 534/53

[56] References Cited

U.S. PATENT DOCUMENTS

| | | | |
|---|---|---|---|
| 3,258,455 | 6/1966 | Natta et al. | 526/103 |
| 3,305,538 | 2/1967 | Natta et al. | 526/103 |
| 3,314,887 | 4/1967 | Carlson | 534/15 |
| 3,364,190 | 1/1968 | Emrick | 526/351 |
| 3,505,369 | 4/1970 | Deffner | 556/53 |
| 3,577,448 | 5/1971 | Deffner | 556/43 |
| 3,893,989 | 7/1975 | Leicht et al. | 526/351 |
| 4,287,328 | 9/1981 | Kikuta et al. | 526/115 |
| 4,316,966 | 2/1982 | Mineshima et al. | 525/53 |
| 4,530,914 | 7/1985 | Ewen et al. | 502/113 |
| 4,794,096 | 12/1988 | Ewen | 502/117 |
| 4,871,704 | 10/1989 | Kohara et al. | 502/117 |
| 4,874,734 | 10/1989 | Kioka et al. | 502/104 |
| 4,892,851 | 1/1990 | Ewen et al. | 502/104 |
| 4,935,474 | 6/1990 | Ewen et al. | 526/114 |
| 4,975,403 | 12/1990 | Ewen | 502/113 |
| 5,017,714 | 5/1991 | Welborn | 556/12 |
| 5,036,034 | 7/1991 | Ewen | 502/117 |
| 5,075,394 | 12/1991 | McDaniel | 502/117 |
| 5,075,426 | 12/1991 | Zielinski | 534/15 |
| 5,120,867 | 6/1992 | Welborn | 556/12 |
| 5,122,583 | 6/1992 | Ewen et al. | 526/125 |
| 5,132,262 | 7/1992 | Rieger et al. | 502/117 |
| 5,155,080 | 10/1992 | Elder et al. | 502/152 |
| 5,223,465 | 6/1993 | Ueki et al. | 502/117 |
| 5,225,500 | 7/1993 | Elder et al. | 526/127 |
| 5,234,878 | 8/1993 | Tsutsui et al. | 502/103 |
| 5,268,495 | 12/1993 | Riepl et al. | 556/11 |
| 5,296,434 | 3/1994 | Karl et al. | 502/117 |
| 5,416,228 | 5/1995 | Ewen et al. | 556/7 |
| 5,459,117 | 10/1995 | Ewen | 502/117 |
| 5,492,983 | 2/1996 | Olonde et al. | 502/104 |
| 5,495,036 | 2/1996 | Wilson et al. | 534/15 |
| 5,539,124 | 7/1996 | Etherton et al. | 548/402 |
| 5,773,638 | 6/1998 | Dawson et al. | 556/52 |
| 5,817,849 | 10/1998 | Wilson et al. | 556/53 |

FOREIGN PATENT DOCUMENTS

| | | |
|---|---|---|
| 2055218 | 11/1991 | Canada . |
| 0227004 | 1/1988 | European Pat. Off. . |
| 0277003 | 1/1988 | European Pat. Off. . |
| 0426638 | 10/1990 | European Pat. Off. . |
| 0427697 | 10/1990 | European Pat. Off. . |
| 0537130 | 9/1992 | European Pat. Off. . |
| 2 488 259 | 2/1982 | France ............... 502/152 |
| 43 37 230 A1 | 5/1995 | Germany . |
| 57-54126 | 3/1982 | Japan ............... 502/152 |
| 63-270313 | 11/1988 | Japan ............... 534/15 |
| 5-310828 | 11/1993 | Japan . |
| 6-73067 | 3/1994 | Japan ............... 534/15 |
| 8-81 516 | 3/1996 | Japan . |
| 801482 | 10/1981 | U.S.S.R. ............... 534/15 |
| 2 274 456 | 7/1994 | United Kingdom ........ 534/15 |
| WO 95/33776 | 12/1995 | WIPO . |
| WO 96/8498A1 | 3/1996 | WIPO . |

OTHER PUBLICATIONS

L. Stahl et al., J.Am.Chem.Soc., 1985, vol. 107, pp. 5016–5018.

R. Ernst, Chem.Rev., vol. 88, No. 7, pp. 1255–1291, Jul. 1988.

S.K. Agarwal et al., J.Inorg.Nuc.Chem., vol. 37, pp. 949–954, Apr. 1975.

Structural Features in Electron Deficient (n–Pentamethylcyclopentadienyl) titanium–Diene Complexes and Their Catalysts in the Selective Oligomerization of Conjugated Diens, Yamamoto, Yasuda, Tatsumi, Lee, Nakamura, Chen, Kai, and Kasai, *Organometallics*, Jan., 1989 8, 105–119.

Bis (2,4–dimethyl pentadienyl)titanium: An Open "Titanocene", Liu and Ernst, *J. Amer Chem Soc.*, 1992, 104, 3737–3739.

Patent Abstracts of Japan, vol. 18, No. 122 (C–1173), Feb. 28, 1994 & JP, A, 05 3/10828 (Mitsubishi).

Constrained–Geometry Titanium (II) Diene Complexes. Structural Diversity and Olefin Polymerization Activity, Devore, Timmers, Hasha, Rosen, Marks, Deck, and Stern, *Organometallics*, 1995, 14, 3132–3134.

Spaleck, W.; Antberg, M.; Rohrmann, J.; Winter, A.; Bachmann, B.; Kiprof, P. Behm, J.; Hermann, W.J.; *Angew. Chem. Int. Ed. Engl.*, 1992, 31, 1347.

(List continued on next page.)

*Primary Examiner*—Mark L. Bell
*Assistant Examiner*—J. Pasterczyk
*Attorney, Agent, or Firm*—Robert W. Strozier

[57] ABSTRACT

New metallocene ligand systems and catalysts/catalyst precursors are described where the ligand system contains at least one open-pentadienyl ligand characterized by an acyclic six π electron delocalized, five atomic center structure. The open pentadienyl ligand is bonded to either another pentadienyl ligand or a Cp ligand by a bridging group. The metal is from group 3–5 or the Lanthanides. These metallocene catalysts/catalyst precursors optionally in combination with co-catalysts can be used to generate a wide variety of different polymer types including HDPE, LLDPE, LHDPE, ethylene/propylene elastomers, tactiospecific C3+ α-olefins, intimate mixture thereof and the like.

19 Claims, No Drawings

OTHER PUBLICATIONS

Mallin, D.T.; Rausch, M.D.; Lin, Y.G.; Dong, S.H.; Chien, J.C.W.; *J Amer. Chem. Soc.*, 1990, 112, 2030.

Jordan, R.F.;Dasher, W.E.; Echols, S.F.,*J. Amer. Chem. Soc.*, 1986, 108, 1718.

Eisch, J.J.; Piotrowski, A.M.; Brownstein, S.K.; Gabe, E.J.; Lee, F.L.; *J. Amer Chem. Soc.*, 107, 7219.

Ewen, J.A.; Jones, R.L.; Razavi, A.; Ferrara, J.D., *J. Amer. Chem. Soc.*, 1988, 110, 6255.

Ewen, J.A., *J. Amer. Chem. Soc.*, 1984, 106, 6355.

Marks, T.J., *Organometallics*, 1988, 7, 1828.

Skattebol, L., Tetrahedron Letters No. 53, pp. 4659–4662 (1969) and *Journal of Organic Chemistry* 29, 2951 (1964).

Yang, X.; Stern, C.L.; Marks, T.J., Amer. Chem Soc. 1991, 113, 3623.

Zambelli, A. et al., "Isotatic Polymerization of Propene: Homogeneous Catalysts Based on Group 4 Metallocenes Without Methylaluminoozane," *Macromolecules*, 1989, 22, pp. 2186–2189.

Farina, M.; Di Sivestro, G.; Sozzani, P., *Macromolecules*, 1982, 15, 1451.

Besancon, J.; Top, S., J. *Organomet. Chem.*, 1977, 127, 139.

Ewen, J.A., "Ligands Effects On Metallocene Catalyzed Ziegler–Natta Polymerization," pp. 271–292.

Coughlin, E.B.; Bercaw, J.E.,*J Amer Chem. Soc.*, 1992, 114, 7606.

Ewen, J.A.; Elder, M.J.; Jones, R.L.;Haspeslagh, L.; Atwood, J.L.; Bott, S.G.;Robinson, K., *Makromol. Chem. Macromol. Symp.*, 1993, 48/49, 253.

Ewen , J.A.;Haspeslagh, K.; Elder, M.J.; Atwood, J.; Zhang, H.; Cheng, H.N., in *Olefin Polymerization*; Kaminsky, W.; Sinn, H.; Eds.; 21–24, Sep. 1987, Springer–Verlag, New York, 1988, p. 271.

Ewen, J.A. Elder, M.J., *Makromol. Chem., Macromol. Symp.* 66, 179–190 (1993).

Ewen, J.A., Elder, M.J., Jones, R.L, Curtis, S., and Cheng H.N., "Syndotactic Propylene Polymerization with iPr[Cp-Flu]$ZrCl_2$", Catalytic Olefin Polymerization Proceedings of the International Symposium on Recent Developments in Olefin Polymerization Catalysts, Tokyo, Oct. 23–25, 1989, 439.

OPEN-PENTADIENYL METALLOCENEN LIGANDS, POLYMERIZATION CATALYSTS/ CATALYST PRECURSORS AND POLYMERS THEREFROM

TECHNICAL FIELD OF THE INVENTION

This invention relates to unique metallocene ligands, catalysts/catalyst precursors, polymers made from the catalysts/catalyst precursors, processes for using the catalysts/catalyst precursors for the production of polymers, and processes for preparing the metallocene ligands and catalysts/catalyst precursors.

More particularly, the present invention relates to new metallocene ligands including at least one open-pentadienyl ligand or group (sometime abbreviated as an Op ligand or group), new polymerization catalysts/catalyst precursors derived therefrom, and products and processes using the polymerization catalysts/catalyst precursors to make atactic and/or tactiospecific homopolymers, atactic and/or tactiospecific copolymers, and/or random or blocked copolymers.

BACKGROUND OF THE INVENTION

Polymerization of vinyl monomer, both mono-olefins and conjugated dienes, has been focused on transition metal catalysts since the work of Ziegler and Natta. These catalysts are based on a central transition metal ion or atom surrounded by a set of coordinating ligands and modified by various co-catalysts. These polymerization systems when brought in contact with addition polymerizable monomers polymerize the monomers into polymers.

By controlling the nature of the ligand system, the central transition metal ion or atom and the co-catalyst, highly active catalytic agents can be made. In addition, catalysts can be made that yield polymers with high degrees of additions regularity and in the case of non-ethylene type monomers, stereoregularity or tactiospecificity.

U.S. Pat. No. 3,051,690 discloses a process of polymerizing olefins to controlled, high molecular weight polymers by the controlled addition of hydrogen to a polymerization system that includes a hydrocarbon insoluble reaction product of a Group IVB, VB, VIB and VIII compound and an alkali metal, alkaline earth metal, zinc, earth metal or rare earth metal organometallic compound. It is further known that certain metallocenes such as bis(cyclopentadienyl) titanium or zirconium dialkyls in combination with aluminum alkyl/water cocatalyst form homogeneous catalyst systems for the polymerization of ethylene.

German Patent Application 2,608,863 discloses the use of a catalyst system for the polymerization of ethylene consisting of bis(cyclopentadienyl) titanium dialkyl, aluminum trialkyl and water. (Cyclopentadienyl is sometimes abbreviated as Cp.) While German Patent Application 2,608,933 discloses an ethylene polymerization catalyst system of the general formula $(Cp)_n ZrR_{4-n}$ where n is a number from 1 to 4 and R is a hydrocarbyl group or a metalloalkyl in combination with an aluminum trialkyl cocatalyst and water.

European Patent Appln. No. 0035242 discloses a process for preparing ethylene and atactic propylene polymers in the presence of a halogen-free Ziegler catalyst system of the general formula $(Cp)_n MR_{4-n}$ where n is an integer from 1 to 4, M is a transition metal, especially zirconium, and R is either hydrogen, a $C_1$–$C_5$ alkyl, metalloalkyl group or a other radical in combination with an alumoxane. While U.S. Pat. No. 5,324,800 discloses a catalyst system for polymerizing olefins including a metallocene catalyst represented by the general formula $(C_5R'_m)_p R''_s (C_5 R'_m) MQ_{3-p}$ and $R''_s (C_5R'_m)_2 MQ'$ where $(C_5R'_m)$ is a substituted Cp group and an alumoxane.

Polyolefins can be prepared in a variety of configurations that correspond to the manner in which each new monomer unit is added to a growing polyolefin chain. Four basic configurations are commonly recognized for polyolefins, atactic, hemi-isotactic, isotactic and syndiotactic. Of course, a given polymer may incorporate regions of each configurational type, yet not exhibit the pure or nearly pure configuration and polyethylene can have no tacticity.

Atactic polymers exhibit no regular order of repeat unit orientation in the polymer chain, i.e., the substituents are not regularly ordered relative to a hypothetical plane containing the polymer backbone (the plane is oriented such that the substituents on the pseudo-asymmetric carbon atoms are either above or below the plane). Instead, atactic polymers exhibit a random distribution of substituent orientations.

Besides metallocene catalysts that produce polyethylene and atactic polyolefins, certain metallocenes are also known to produce polymers with varying degrees of stereoregularity or tactiospecificity, such as isotactic, syndiotactic, and hemi-isotactic polymers which have unique and regular repeating stereochemistries or substituent orientations relative to the plane containing the polymer backbone.

Isotactic polymers are typically described as having the substituents attached to the pseudo-asymmetric carbon atoms oriented on the same side relative to the polymer backbone, i.e., the substituents are all either configured above or below a plane containing the polymer backbone. Isotacticity can be determined through the use of NMR. In Bovey's NMR nomenclature, an isotactic pentad is represented by . . . mmmm . . . with each "m" representing a "meso" dyad or successive monomer units oriented with the substituents oriented on the same side relative to the polymer backbone. As is well known in the art, any deviation, disruption, or inversion about a pseudo asymmetric carbon in the chain will lower the degree of isotacticity and crystallinity of the polymer.

In contrast, the syndiotactic structure is typically described as having the substituents, that are attached to the pseudo-asymmetric carbon atoms, pseudo-enantiomorphically disposed, i.e., the substituents are oriented alternately and regularly above and below the plane containing the polymer chain. Syndiotacticity can also be determined through the use of NMR. In NMR nomenclature, a syndiotactic pentad is represented by . . . rrrr . . . in which each "r" represents a "racemic" dyad, i.e., successive substituents on alternate sides of the plane. The percentage of "r" dyads in the chain determines the degree of syndiotacticity of the polymer.

There are other variations in polymer structures as well. One such variant is the so-called hemi-isotactic polymers. Hemi-isotactic polymers are ones in which every other pseudo-asymmetric carbon atom has its substituent oriented on the same side relative to the plane containing the polymer backbone. While, the other pseudo-asymmetric carbon atoms can have their substituents oriented randomly either above or below the plane. Since only every other pseudo-asymmetric carbon is in an isotactic configuration, the term hemi is applied.

Isotactic and syndiotactic polymers are crystalline polymers and are insoluble in cold xylene. Crystallinity distinguishes both syndiotactic and isotactic polymers from hemi-isotactic or atactic polymers that are soluble in cold xylene and are non-crystalline. While it is possible for a catalyst to produce all four types of polymers (atactic, hemi-isotactic, isotactic and syndiotactic), it is desirable for a catalyst to produce predominantly or essentially polymer type with little or no other polymer type and few stereochemical defects.

Several catalysts that produce isotactic polyolefins are disclosed in U.S. Pat. Nos. 4,794,096 and 4,975,403, as well as European Pat. Appln. 0,537,130. Several catalysts that produce syndiotactic polyolefins are disclosed in U.S. Pat. Nos. 3,258,455, 3,305,538, 3,364,190, 4,852,851, 5,155,080, and 5,225,500.

Besides neutral metallocenes, cationic metallocenes are known to result in polymers with varying degrees of tactiospecificity. Cationic metallocene catalysts are disclosed in European Patent Applications 277,003 and 277,004. Catalysts that produce hemi-isotactic polyolefins are disclosed in U.S. Pat. No. 5,036,034.

In addition to monoolefins homopolymers, polymerization catalysts for preparing copolymers of monoolefins or polymers of di-functional olefins or copolymers of di-functional olefins and monoolefins can be prepared using coordinated metal catalysts including metallocene catalysts.

Although many metallocene catalysts are now available, the need for new ligand systems to make metallocene catalysts for the polymerization of olefins is still important and represents a significant advancement in the art. Such new ligand systems and the catalyst derived therefrom can offer new design approaches for making highly stereoregular or tactiospecific polymers essentially free of defects, polymers with controlled defect statistics, copolymers with controlled properties, new approaches for molecular weight control and the control of other polymer properties.

SUMMARY OF THE INVENTION

The present invention provides new open-pentadienyl containing metallocene ligand systems and metallocene catalysts/catalyst precursors derived therefrom for the polymerization of addition polymerizable monomers where the catalyst/catalyst precursors can be used to prepare polymer products with desired properties such as molecular weight, molecular weight distribution, density, tacticity and terminal unsaturation.

The catalysts of the present invention are useful for the polymerization of addition polymerizable monomers such as α-olefins to homopolymer and/or copolymers and comprise new metallocene catalysts optionally in combination with co-catalysts such as alumoxanes. The metallocenes of the present invention are organometallic coordination compounds of mono, di and tri-open-pentadienyl ligand systems and their transition metals coordinate complexes, especially complexes of a Group 3, 4, or 5 elements from the Periodic Table of Elements, or Lu, La, Nd, Sm, Gd, and the like.

The metallocenes of the present invention include metallocenes represented by the general formula $Z'R''_iZ_iMQ_kA_l$, where Z' is an open-pentadienyl radical (sometime abbreviated as a Op radical) of formula (a):

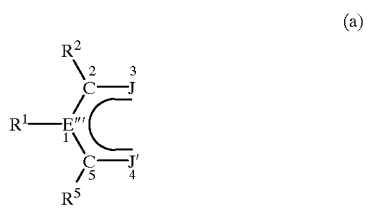

where: E''' is a carbon atom, a nitrogen atom, a silicon atom or a phosphorus atom; J and J' are the same or different and where J is a $CR^3R^{3'}$ radical, a $SiR^3R^{3'}$ radical, a $NR^{3''}$ radical, a $PR^{3''}$ radical, an oxygen atom or a sulfur atom and J' is a $CR^4R^{4'}$ radical, a $SiR^4R^{4'}$ radical, a $NR^{4''}$ radical, a $PR^{4''}$ radical, an oxygen atom or a sulfur atom and where J and J' can be the same or different; $R^1$, $R^2$, $R^3$, $R^{3'}$, $R^{3''}$, $R^4$, $R^{4'}$, $R^{4''}$, and $R^5$ can be the same or different and are a hydrogen atom, a linear or branched $C_1$–$C_{20}$ hydrocarbyl radical, a linear or branched $C_1$–$C_{20}$ halocarbyl radical, a linear or branched $C_1$–$C_{20}$ hydrohalocarbyl radicals, a linear or branched $C_1$–$C_{20}$ alkoxy radical, a $C_3$–$C_{12}$ cyclohydrocarbyl radical, a $C_3$–$C_{12}$ cyclohydrohalocarbyl radical, an aryl radical, an alkylaryl radical, an arylalkyl radical, a silicon hydrocarbyl radical, a germanium hydrocarbyl radical, a phosphorous hydrocarbyl radical, a nitrogen hydrocarbyl radical, a boron hydrocarbyl radical, an aluminum hydrocarbyl radical, a halogen atom, and the like or $R^2$ and $R^3$, $R^{3'}$ or $R^{3''}$ and/or $R^5$ and $R^4$, $R^{4'}$ or $R^{4''}$ can be joined together to form a $C_4$ to $C_6$ ring or a fused ring systems containing 6 to 20 carbon atoms or where $R^3$, $R^{3'}$, or $R^{3''}$ and $R^4$, $R^{4'}$, or $R^{4''}$ can be joined together so that the five numbered atomic centers making up the five centered delocalized six π electron ligand are contained in a $C_7$ to $C_{20}$ ring; Z is the same of different Op containing radical, a Cp containing radical, a nitrogen containing radical, a phosphorous containing radical, an oxygen containing radical, a sulfur containing radical, or the like.

R'' is a $C_1$–$C_{20}$ alkenyl radical, a peralkylated $C_1$–$C_{20}$ alkenyl radical, a $C_3$–$C_{12}$ cyclohydrocarbyl radical, an aryl radical, a diaryl allyl radical, a silicon hydrocarbyl radical including a dihydrocarbyl silenyl radical, a germanium hydrocarbyl radical including a dihydrocarbyl germanium radical, a phosphorous hydrocarbyl radical including a phosphine radical, a nitrogen hydrocarbyl radical including an amine radical, a boron hydrocarbyl radical, an aluminum hydrocarbyl radical, or the like, and where R'' structurally bridges the Z' and Z groups.

M is a Group 3, 4, or 5 element from the Periodic Table of Elements, or Lu, La, Nd, Sm, Gd, or the like; Q is a $C_1$–$C_{20}$ hydrocarbon radical such as an aryl, alkyl, alkenyl, alkylaryl, or arylalkyl radical or a halogen atom; A is a stable non-coordinating or pseudo-non-coordinating anion; i is an integer having a value of 0 or 1; j is an integer having a value from 0 to 2; k is an integer having a value from 1 to 3; and l is an integer having a value from 0 to 2.

The present invention further provides a process for polymerizing polymerizable monomers comprising contacting at least one of the catalyst components of the general formula $Z'R''_iZ_iMQ_kA_l$ with at least one polymerizable monomer. In addition, a co-catalyst such as an alkyl aluminum or a alumoxane may be present as well or may be combined with the metallocenes prior to bring the catalytic system in contact with the monomer. For cationic catalysts of the general formula (i.e., l=1 or 2), an ion-pair or a strong Lewis acid compound is reacted with the neutral metallocene (i.e., 0 l=0) to form a cationic metallocene either prior to or concurrent with contacting the catalytic system with monomer.

The present invention further provides a process for producing tactiospecific polymers comprising contacting at least one catalyst component of the general formula $Z'R''_iZ_jMQ_kA_l$, where i is 1, j is 1, and Z' and Z are as previously described and further where Z' and Z bear similar or different substituents in the $\alpha$ and $\beta$ positions such that at least one $\beta$ substituent is sterically bulkier than a hydrogen atom and particularly sterically bulkier than a methyl group. Metallocenes of the present invention where neither Z' or Z are bilaterally or pseudo-bilaterally symmetric or where only one of them is bilaterally or pseudo-bilaterally symmetric and with the bulky $\beta$ is on the non symmetric Z' or Z radical will yield isoselective catalsyts. Such isoselective catalyst generally have overall $C_2$ or pseudo-$C_2$ symmetry as well. Metallocenes of the present invention where Z' and Z are bilaterally or pseudo-bilaterally symmetric and have the bulky group on only one Z' or Z will yield syndioselective catalysts and have overall $C_s$, or pseudo-$C_s$ symmetry Furthermore, the catalyst components of the general formula may be made into pre-polymerized catalytic systems prior to contacting the system with the monomer and/or prior to the stabilization of the reaction conditions.

Moreover, the present invention can also be practiced to produce intimate blends of different types of polymers by contacting a catalyst of the general formula designed for each polymer type with one or more monomers. The preferred application of this invention is in the production of polyethylene, polyethylene copolymers, polypropylene, polypropylene copolymers, isotacticpolypropylene, syndiotactic polypropylene, hemi-isotactic polypropylene, or mixtures thereof.

The present invention also includes methods for preparing the new ligand systems which include at least one open-pentodienyl ligand, methods for preparing the catalysts/catalyst precursor of the general formula, and methods for activating the catalysts/catalyst precursors of the general formula into catalytically active polymerization agents.

DETAILED DESCRIPTION OF THE INVENTION

The inventors have found that a new class of metallocene catalyst with wide application to the production of polymers of addition polymerizable monomers can be formed utilizing ligand systems containing at least one and up to three open-pentadienyl ligands where the open-pentadienyl ligands are delocalized, six $\pi$ electron systems that are not constrained to a five membered ring.

The present invention is directed towards catalytic systems and catalytic processes for the polymerization of addition polymerizable monomers. In particular, the present invention is directed towards catalytic systems and processes for the polymerization of polymerizable vinyl monomers, including $\alpha$-olefins such as ethylene, propylene, butylene, and the like to polymers such as high molecular weight polyethylenes including linear low density polyethylene (LLDPE) and high density polyethylene (HDPE), polypropylene, isotactic polypropylene, syndiotactic polypropylene, hemi-isotactic polypropylene and the like and intimate mixtures thereof. The polymers are intended for fabrication into articles by extrusion, injection molding, thermoforming, rotational molding, and the like.

In particular, the polymers of this invention include homopolymers of ethylene, propylene, butylene, styrene, and other vinyl monomers and copolymers of these vinyl monomers where the vinyl monomers can have from 2 to about 20 carbon atoms and preferably 2 to 12 carbon atoms.

In the process of the present invention, a monomer such as ethylene or propylene, either alone or together with other $C_2$–$C_{20}$ monomers, is polymerized in the presence of a catalyst system comprising at least one metallocene containing at least one Op ligand and optionally a co-catalyst such as an alumoxane.

In accordance with this invention, one can also produce olefin copolymers particularly copolymers of ethylene and/or propylene and other olefins by a judicious choice of metallocenes of the general formula. The choice of metallocenes of the present invention can be used to control comonomer content as well as other properties of the polymer such as tacticity for vinyl monomers other than ethylene or ethylene like monomers.

The new metallocene compounds in accordance with the present invention are mono-, bi- and/or tri-open-pentadienyl metal compounds. The metallocenes of the present invention include those represented by the general formula $Z'R''_iZ_jMQ_kP_l$, where: Z' is a open-pentadienyl radical of formulas (a):

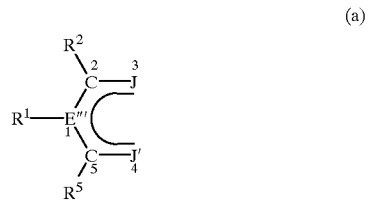

(a)

where: E''' is a carbon atom, a nitrogen atom, a silicon atom or a phosphorus atom; J and J' are the same or different and where J is a $CR^3R^{3'}$ radical, a $NR^{3''}$ radical, a $PR^{3''}$ radical, an oxygen atom or a sulfur atom and J' is a $CR^4R^{4'}$ radical, a $NR^{4''}$ radical, a $PR^{4''}$ radical, an oxygen atom or a sulfur atom; $R^1$, $R^2$, $R^3$, $R^{3'}$, $R^{3''}$, $R^4$, $R^{4'}$, $R^{4''}$, and $R^5$ can be the same or different and are a hydrogen atom, a linear or branched $C_1$–$C_{20}$ hydrocarbyl radical, a linear or branched $C_1$–$C_{20}$ halocarbyl radical, a linear or branded $C_1$–$C_{20}$ hydrohalocarbyl radicals, a linear or branched $C_1$–$C_{20}$ alkoxy radical, a $C_3$–$C_{12}$ cyclohydrocarbyl radical, a $C_3$–$C_{12}$ cyclohydrohalocarbyl radical, an aryl radical, an alkylaryl radical, an arylalkyl radical, a silicon hydrocarbyl radical, a germanium hydrocarbyl radical, a phosphorous hydrocarbyl radical, a nitrogen hydrocarbyl radical, a boron hydrocarbyl radical, an aluminum hydrocarbyl radical, a halogen atom, and the like or $R^2$ and $R^3$, $R^{3'}$ or $R^{3''}$ and/or $R^5$ and $R^4$, $R^{4'}$ or $R^{4''}$ can be joined together to form a $C_4$ to $C_6$ ring or a fused ring systems containing 6 to 20 carbon atoms ring or where $R^3$, $R^{3'}$, or $R^{3''}$ and $R^4$, $R^{4'}$, or $R^{4''}$ can be joined together so that the five numbered atonic centers making up the five centered delocalized six $\pi$ electron ligand are contained in a $C_7$ to $C_{20}$ ring; Z is the same of different Op containing radical, a Cp containing radical, a nitrogen containing radical, a phosphorous containing radical, an oxygen containing radical, a sulfur containing radical, or the like; R'' is a $C_1$–$C_{20}$ alkenyl radical, a peralkylated $C_1$–$C_{20}$ alkenyl radical, a $C_3$–$C_{12}$ cyclohydrocarbyl radical, an aryl radical, a diaryl allyl radical, a silicon hydrocarbyl radical including a dihydrocarbyl silenyl radical, a germanium hydrocarbyl radical including a dihydrocarbyl germanium radical, a phosphorous hydrocarbyl radical including a phosphine radical, a nitrogen hydrocarbyl radical including an amine radical, a boron hydrocarbyl radical, an aluminum hydrocarbyl radical, and the like where R'' structurally bridges the Z' and Z groups; M is a Group 3, 4, or 5 elements from the Periodic Table of Elements, or Lu, La, Nd, Sm, Gd, and the like; Q is a linear or branched alkyl radical, an aryl radical, an alkenyl, an alkylaryl, an arylalkyl radical or a halogen atom; A is a stable anion; i is an integer having a value of 0 or 1; j is an integer having a value from 0 to 2; k is an integer having a value from 1 to 3; and l is an integer having a value from 0 to 2.

The term open-pentadienyl is intended to refer to all six π electron structures that are centered on five connected atoms in an all cis configuration, but where the five atoms bearing the six π electrons are not part of a five membered ring, i.e., the five atoms do not form a cyclopentyl ring system. Of course, all five atoms should preferably be $sp_2$ hybridized or in some other hybridization that can support electron delocalization.

One possible precursor to the Op ligands of this invention is a precursor where four of the atomic centers are part of two non-conjugated double bonds connected to and separated by a central atom, where the double bonds contribute two electron each to the ligand system while the central atom supplies two electrons to the system either directly as a lone pair of a N or P atom or through the loss of a removable group, such as a proton, to result in the formation of an anionic center as for a C or Si atom. Of course, other central species could be used as well including Ge, As and the like.

The numbers associated with the five atomic centers in formula (a) are there to indicate how substituent positions will be addressed in the remainder of the specification which is analogous to the numbering in cyclopentadiene, but not to the IUPAC numbering convention for non-ring systems. Thus, for those metallocenes having a structural bridge, the structural bridge will be bonded to the central atom which is designated as position 1, in a fashion analogous to the numbering in cyclopentadiene. Additionally, the 2 and 5 positions will sometimes be jointly referred to as the α positions or proximal positions (proximal to the 1 position), while the 3 and 4 positions will sometimes be jointly referred to as the β or distal positions.

Open-pentadienyl ligands with one or two aromatic rings or ring systems supplying one or two pairs of electrons to the six π electron system form groups that are open analogs of such cyclic group as indene or fluorene ring systems as well as other open analogs of other aromatic species. These analogous open systems will be designated with an o-followed by a name or abbreviated name such as o-Ind (open-indene) and o-Flu (open-fluorene).

A particularly important subclass of ligand systems and catalysts/catalyst precursors derived therefrom of this invention are represented by the formula Z'R"ZMQ$_k$A$_l$ where Z' is a open-pentadienyl radical as described above, Z is the a Cp containing radical, a nitrogen containing radical, a phosphorous containing radical, an oxygen containing radical, a sulfur containing radical, or the like Another important subclass of ligand systems and catalysts/catalyst precursors derived therefrom of this invention are represented by the formula Z'R"Z'MQ$_k$A$_l$, where Z' is the same or different Op containing radical as described above, and where R", Me, Q, P, k, and l are as described above.

Yet, another important subclass of ligand systems and catalysts/catalyst precursors derived therefrom of this invention capable of producing polymers with varying degrees of tacticity are represented by the formula Z'R"ZMQ$_k$A$_l$, where Z' is a Op containing radical and Z is the same or different Op containing radical, a Cp containing radial, a nitrogen containing radical, a phosphorous containing radical, an oxygen containing radical, or a sulfur containing radical and where Z' and Z are substituted with at least one non-hydrogen substituent so that the overall ligand or catalysts system has either $C_s$, $C_2$, pseudo-$C_s$, or pseudo-$C_2$ symmetry and R", M, Q, A, k, and I are as described above.

The present invention also provides a process for producing polymers and copolymers having varying and controllable properties including a high molecular weight at relatively high temperatures, tactiospecificity, low, medium and high molecular weights, stereoregularity, narrow or broad molecular weight distribution, etc. The process comprises polymerizing one or more monomers in the presence of one or more of the metallocenes described above. The advantages and novelties of this invention are obtained by the presence of a least one open-pentadienyl containing ligands in conjunction with other ligands to prepare new metallocenes and catalysts therefrom in order to control and tailor polymer properties such as molecular weight, copolymer composition, molecular weight distribution, crystallinity, tacticity, melting point, T$_g$, etc.

The inventors have found that catalysts of the present invention can also be prepared which yield stereoregular and/or stereospecific polymer products such as linear high molecular weight polyethylene, isotactic polyolefins, syndiotactic polyolefins and hemi-isotactic polyolefins. These uniquely designed catalysts have as a key feature a ligand system containing two ligands, at least one being a Op ligand and for tactio specific catalysts a given symmetry or pseudo-symmetry.

For stereospecific and/or tactiospecific polyolefins, the catalysts of the present invention can be stereolocked and preferably stereorigid or geometrically constrained, in the case where the second ligand is a non-Cp or non-open-pentadienyl ligand, through the judicious choice of substituents and bridging groups where the substituents lock the polymer chain-end orientation and/or monomer approach such that each successive monomer addition is stereospecific or where the degree of stereoselectivity can be controlled. These catalyst are characterized by having two ligands (i.e., j=1) and where at least one β or distal substituent or their equivalent (the group on a amine or phosphine anion ligand) on one ligand is sterically different from the β substituents on the other ligand and such that the overall ligand system has either $C_s$, $C_2$, pseudo-$C_s$, or pseudo-$C_2$ symmetry.

The inventors have also found that by controlling the substituents relative steric size, catalysts can be formed that insert statistically controllable defects into the resulting polymers. The inventors have also found that catalysts of the present invention can be designed to produce hemi-isotactic polymers. The inventors have also found that intimate mixtures of polymers with different properties can be prepared by polymerizing monomer in the presence of a combination of catalysts of the present invention or polymerizing monomer in the presence of catalysts of this invention in combination with prior art catalysts.

Traditionally, the term metallocene, in accordance with normal art usage, denotes an organometallic coordination compound in which two cyclopentadienyl containing ligands are coordinated to or "sandwiched" about a central metal species and where all five centers of the Cp ring are involved in metal coordination (hapta five coordinate ligands). The metal species may be a transition metal or transition metal halide, alkylide, alkoxide, or the like. Such structures are sometimes referred to as "molecular sandwiches" since the cyclopentadienyl ligands are oriented above and below a plane containing the central coordinated metal atom and nearly parallel to the planes containing the Cp ring. Similarly, the term "cationic metallocene" means a metallocene in which the central coordinated metal atom carries a positive charge, i.e., the metallocene complex is a cation associated with a stable non-coordinating or pseudo-non-coordinating anion.

However, in additions to the traditional meaning of the term metallocene, the present invention expands this term to encompass ligand systems were at least one of the ligands coordinating the central metal atom or ion is an open-pentadienyl containing ligand and the second ligand can be another Op containing ligand, a Cp containing ligand, or a nitrogen, phosphorus, oxygen or sulfur containing ligand.

The metallocenes of the present invention can be either non-stereorigid/non-stereolocked, stereorigid/non-stereolocked, non-stereorigid/stereolocked, stereorigid/stereolocked, or mixtures thereof. Stereorigidity is imparted to the metallocene ligand systems of this invention by a chemical bridging group (R") connecting the two ligands making up the metallocene, i.e., i=1. The bridging group prevents the two ligands from undergoing structural isomerizations.

Suitable Z radicals for use in the present invention include, without limitation, radicals represented as follows: (1) Cp containing radicals represented by the general formula $(C_5R'_m)$ where $(C_5R'_m)$ is a cyclopentadienyl or substituted cyclopentadienyl radical, each R' is the same or different radicals as described above for radicals $R^1$–$R^5$ or where two carbon atoms are joined together to form a $C_4$–$C_6$ ring and m an integer having a value from 0 to 5; (2) nitrogen and phosphorus containing radicals represented by the general formula $(ER^6_m)$ where E is nitrogen or phosphorus atom, each $R^6$ is same or different radical as described above for radicals $R^1$–$R^5$ and m is an integer having a value from 1 to 3 (when n is 1, E carries a negative charge); (3) an oxygen or sulfur containing radical represented by the general formula $(ER^7_n)$ where E is oxygen or sulfur atom and where $R^7$ is a radical as described above for radicals $R^1$–$R^5$ and n is an integer having a value of 0 or 2 (when n is 0, then E carries a negative charge); or (4) Op containing radicals with formula (a) described above.

Of course, one skilled in the art should also recognize that the permissible values for i, j, k, l, m, and n will depend on the actual ligand system and on the coordinating metal and these values are understood to conform to known organometallic structural and electronic requirements.

Suitable structural bridging groups R" for use in this invention and impart stereorigidity to the metallocene catalysts of this invention include, without limitation, a $C_1$–$C_{20}$ alkenyl radical, a peralkylated $C_1$–$C_{20}$ alkenyl radical, a dialkyl methyl radical, a $C_3$–$C_{12}$ cyclohydrocarbyl radical, an aryl radical, a diarylmethylene radical, a diaryl allyl radical, a silicon hydrocarbyl radical, dihydrocarbyl silenyl radicals, a germanium hydrocarbyl radical, a phosphorous hydrocarbyl radical, a nitrogen hydrocarbyl radical, a boron hydrocarbyl radical, an aluminum hydrocarbyl radical, and the like.

Other suitable bridging groups R", include ionic units such as $B(C_6F_5)_2$, and $Al(C_6F_5)_2$, and the like and $R_2C$, $R_2Si$, $R_4Et$, $R_6Pr$, and the like where R can be any hydrocarbon, cyclic hydrocarbon, cyclic or linear hydrocarbons bearing another organometallic catalyst or carboranes, etc. Indeed, the bridges can be $C_2$ bridges (and $C_3$ etc.) which form the backbone of polymeric supports (e.g. the atactic, syndiotactic and isotactic polymers from vinylindene and 9-vinyl-fluorene etc.) as well as functionalized polystyrene precursors and all other polymers with terminal or branched boron or Al functional groups which are bonded to the catalysts, e.g., in zwitterionic form. $R_2C$ and $R_2Si$ bridging groups are preferred with isopropylidene and dimethylsilenyl bridging groups being particularly preferred.

Suitable radicals corresponding to $R^1$ through $R^7$ and R' include, without limitation, hydrogen atoms, linear or branched $C_1$–$C_{20}$ hydrocarbyl radicals, linear or branched $C_1$–$C_{20}$ halocarbyl radicals, linear or branched $C_1$–$C_{20}$ hydrohalocarbyl radicals, linear or branched $C_1$–$C_{20}$ alkoxy radicals, $C_3$–$C_{12}$ cyclohydrocarbyl radicals, a $C_3$–$C_{12}$ cyclohydrohalocarbyl radicals, aryl radicals, alkylaryl radicals, arylalkyl radicals, silicon hydrocarbyl radicals, germanium hydrocarbyl radicals, phosphorus hydrocarbyl radicals, nitrogen hydrocarbyl radicals, boron hydrocarbyl radicals, aluminum hydrocarbyl radicals, halogen atoms, and the like. Preferable, non-hydrogen radicals include linear or branched $C_1$–$C_{20}$ alkyl radicals with linear or branched $C_1$–$C_{10}$ radicals being particularly preferred and methyl, ethyl, isopropyl, t-butyl, and tri-alhylsilyl radicals being especially preferred.

Additionally, suitable radicals corresponding to $R^1$ through $R^7$ and R' include, without limitation, zwitterionic radicals such as Cp—$B(C_6F_5)_{3-}$, Cp—$Al(C_6F_5)_3^-$, Cp—Al $(CF_3)_3^-$, Cp—X—$Al(C_6F_5)_3^-$, Cp—X—$B(C_6F_5)_3^-$, and the like are also suitable radicals, where X can represent an alkenyl group, alkenoxy group or the like. Metallocenes of this invention containing zwitterionic radicals on either one of the ligand making up the ligand system of the present invention and incorporating a group 4 metal for M would not need an independent and sometimes stereochemically interfering counterion (i.e., l=0). These zwitterionic radicals may also be suitable for mono and di cations of catalysts of formula (I) where M is a group metal in the plus five oxidation state (M(V)). They could even conceivably be used to create ion-pair catalysts with the normally neutral group 3 metals in the plus three oxidation state (Me(III)). In this case, one could obtain heterogeneous insoluble ion-pair systems for improved polymer particle size and morphology control.

Suitable metals corresponding to M include, without limitation, Group 3, 4, or 5 elements from the Periodic Table of Elements, or Lu, La, Nd, Sm, Gd, and the like. Preferably, M is a Group 4 or 5 metal and more preferably a Group 4 metal, and specifically titanium, zirconium or hafnium.

Suitable hydrocarbyl radical or halogen corresponding to Q include, without limitation, a linear or branched $C_1$–$C_{20}$ alkyl radical, an aryl radical, an alkylaryl radical, an arylalkyl radical, a F atom, a Cl atom, a Br atom, and an I atom. Q is preferably a methyl or halogen, and more particularly a chlorine atom.

Exemplary hydrocarbyl radicals are methyl, ethyl, propyl, butyl, amyl, isoamyl, hexyl, isobutyl, heptyl, octyl, nonyl, decyl, cetyl, 2-ethylhexyl, phenyl, and the like. Exemplary alkylene radicals are methylene, ethylene, propylene, isopropylidenel, and the like. Exemplary halogen atoms include fluorine chlorine, bromine and iodine and of these halogen atoms, chlorine is preferred. Exemplary of the alkylidene radicals is methylidene, ethylidene and propylidene. Exemplary nitrogen containing radicals include amines such as alkyl amines, aryl amines, arylalkyl amines, and alkylaryl amines. Exemplary silyl containing radicals include, dialkyl silenyl, trialkyl silyl and the like.

Suitable non-coordinating or pseudo-non-coordinating anions corresponding to P in the general formula (I) include, without limitation, $[BF_4]^-$, $B(PhF_5)^-_4$, $[W(PhF_5)_6]^-$, $[Mo(PhF_5)_6]^-$ (wherein $PhF_5$ is pentafluorophenyl), $[ClO_4]^-$, $[S_nO_6]^-$, $[PF_6]^-$, $[SbR_6]^-$, $[AlR_4]^-$ (wherein each R is independently, a $C_1$–$C_5$ alkyl group preferably a methyl group, an aryl group, e.g. a phenyl or substituted phenyl group, or a fluorinated aryl and alkyl group).

Tactiospecific metallocenes of the present invention (i.e., metallocenes that produce polymers with varying degrees of tacticity) are metallocenes of the general formula where i=1 and j=1 and are characterized by having $C_2$ or pseudo-$C_2$ for isoselective catalyst or $C_s$ or pseudo-$C_s$ symmetry for syndio selective catalyst with respect to the distribution with α and β substituents (or pseudo α and β substituents in the case of non Cp or Op ligands) in the ligand system. Said another way, $C_s$ or pseudo-$C_s$ symmetry is manifest in ligand systems where both Z' and Z have bilateral or pseudo-bilateral symmetry with respect to a bisecting mirror plane. While, $C_2$ and pseudo-$C_2$ symmetry is manifest in ligand systems where only one ligands (i.e., Z' or Z) has bilateral or pseudo-bilateral symmetry and the other ligand is not bilaterally or pseudo bilaterally symmetric. Preferably, at least one of the β substituents on of at least one of the ligands in the bridged metallocenes of the present invention should be sterically larger than hydrogen and particularly sterically larger than a methyl group. All substituents except possibly with the exception of fluorine, are sterically larger than hydrogen for the purposes of this invention and fluorine is considered larger than hydrogen for the purposes of this invention as well. Most substituents are also sterically bulkier than a methyl group and in particular all substituents with more than one atom with an atomic number greater than or equal to carbon or with two or more atoms with atomic numbers greater than or equal to boron are considered sterically bulkier than a methyl group.

By the term "bi-lateral symmetry" as used here, is meant the symmetry of the ligand as viewed through the axes of the substituted and un-substituted Cp groups. For example, the isopropylidene (cyclopentadienyl-1-fluorenyl) ligand would exhibit such bilateral symmetry whereas the corresponding structure but with the cyclopentadienyl group substituted at the three position would not exhibit bilateral symmetry. The ligand with two identical substituents at the 3 and 4 position on the cyclopentadienyl group would have bilateral symmetry.

Of the metallocenes of this invention, hafnocenes, zirconocenes and titanocenes are most preferred. Illustrative, but non-limiting, examples of these metallocenes which can be usefully employed in accordance with this invention are mono-open-pentadienyl titanocenes such as, open-pentadienyl titanium trichloride and substituted-open-pentadienyl titanium trichloride (i.e., $R^1$, $R^2$, $R^3$, $R^{3'}$, $R^4$, $R^{4'}$ and $R^5$ are hydrogens, halogens, alkyls, haloalkyls, hydrohaloalkyls, and the like in the case of an all carbon Op ligands; $R^1$, $R^2$, $R^{3''}$, $R^{4''}$, and $R^5$ are hydrogens, alkyls, haloalkyls, hydrohaloalkyls, and the like in the case of the diimino (C=NR) or diphosphino (C=PR) Op ligands; and $R^1$, $R^2$, and $R_5$ are hydrogens, alkyls, haloalkyls, hydrohaloalkyls, and the like in the case of carbonyl (C=O) or thiocarbonyl (C=S) Op ligands), bis(open-pentadienyl) titanium diphenyl where the open-pentadienyl radical can be unsubstituted or substituted, carbenes represented by the formulas $Op_2Ti=CH_2$ $Al(CH_3)_2Cl$, $(Op)(Cp)Ti=CH_2$ $Al(CH_3)_2Cl$, $(Op)(E'R^6{}_m)Ti=CH_2$ $Al(CH_3)_2Cl$ or $(Op)(ER^7{}_n)Ti=CH_2$ $Al(CH_3)_2Cl$, and derivatives of these reagents where the titanium moeity is $Ti=CH_2$ $Al(CH_3)_3$, $(TiCH_2)_2$, $Ti=CH_2$ $AlR_2Cl$, wherein Op is an open-pentadieny ligand or a substituted open-pentadienyl ligand, Cp is a cyclopentadienyl or substituted cylopentadienyl radical, and R is an alkyl, aryl or alkylaryl radical having from 1–18 carbon atoms; substituted bis(Op)Ti(IV), (Op)(Cp)Ti(IV), $(Op)(E'R^6{}_m)Ti(IV)$ or $(Op)(ER7{}_n)Ti(IV)$ or compounds such as bis(o-Ind)Ti, (Ind)(o-Ind)Ti, (o-Ind)$(ER^6{}_m)$Ti or (o-Ind)$(ER^7{}_n)$Ti diphenyl or dichloride, bis(o-Flu)Ti, (o-Flu)(Flu)Ti, (o-Flu)$(ER^6{}_m)$Ti or (o-Flu)$(ER7{}_n)$Ti diphenyl or dihalides and other dihalide complexes where $R^6$, $R^7$, m and n are as described previously; multiply substituted Op systems and multiply substituted Op and multiply substituted Cp or $E'R^6{}_m$ or $ER^7{}_n$ mixed systems such as bis(1,2-dimethyl-Op)Ti diphenyl or dichloride, bis (1,2-diethyl-open-Op)Ti diphenyl or dichloride and other dihalide complexes; silicone, phosphine, amine or carbon bridged Op containing ligand system complexes, such as dimethyl silyl bis(Op), (Op)(Cp), $(Op)(E'R^6{}_m)$ or $(Op)(ER^7{}_n)$ titanium diphenyl or dichloride, methyl phosphine bis(Op), (Op)(Cp), $(Op)(E'R^6{}_m)$ or $(op)(XR^7{}_n)$ titanium diphenyl or dichloride, methylene bis-(Op), (Op)(Cp), (Op)$(E'R^6{}_m)$ or $(Op)(ER^7{}_n)$ titanium diphenyl or dichloride, ethylene bis(4,5,6,7-tetrahydro-O-Ind), (4,5,6,7-tetrahydroindenyl)(4,5,6,7-tetrahydro-O-Ind), (4,5,6,7-tetrahydro-O-Ind)$(E'R^6{}_m)$ or (4,5,6,7-tetrahydro-O-Ind)$(ER^7{}_n)$ titanium dichloride and other dihalide complexes and the like.

Illustrative, but non-limiting, examples of the zirconocenes which can be usefully employed in accordance with this invention are mono-open-pentadienyl zirconocenes such as, open-pentadienyl zirconium trichloride and substituted-open-pentadienyl zirconium trichloride (i.e., $R^1$, $R^2$, $R^3$, $R^{3'}$, $R^4$, $R^{4'}$ and $R^5$ are hydrogens, halogens, alkyls, haloalkyls, hydrohaloalkyls, and the like in the case of an all carbon Op ligands; $R^1$, $R^2$, $R^{3''}$, $R^{4''}$, and $R^5$ are hydrogens, alkyls, haloalkyls, hydrohaloalkyls, and the like in the case of the diimino (C=NR) or diphosphino (C=PR) Op ligands; and $R^1$, $R^2$, and $R^5$ are hydrogens, alkyls, haloalkyls, hydrohaloalkyls, and the like in the case of carbonyl (C=O) or thiocarbonyl (C=S) Op ligands), bis(Op), (Op)(Cp), (Op)$(E'R^6{}_m)$, or $(Op)(ER^7{}_n)$ zirconium diphenyl or dimethyl or dihalide, all substituted analogs thereof; silicone, phosphorus, and carbon bridged analogs such as dimethylsilyl bis(Op), (Op)(Cp), $(Op)(E'R^6{}_m)$ or $(op)(ER^7{}_n)$ zirconium dimethyl or dihalide, methylphosphine bis(Op), (Op) (Cp), $(Op)(E'R^6{}_m)$ or $(Op)(ER^7{}_n)$ zirconium dimethyl or dihalide, and methylene bis(Op), (Op)(Cp), $(Op)(ER^6{}_m)$ or $(Op)(ER^7{}_n)$ zirconium dimethyl or dihalide, carbenes represented by the formula bis(Op), (Op)(Cp), $(Op)(E'R^6{}_m)$ or $(Op)(ER^7{}_n)$ $Zr=CH_2P(C_6H_5)_2CH_3$, and derivatives of thereof.

The present invention also encompasses Hf, La, Lu, Sm, Nd, and Gd analogs of the above zirconocenes and titanocenes.

A few exemplified but not-limiting examples of metallocene ligands (R"Z'Z) that generate catalysts with varying degrees of isotactic selectivity would include, without limitation: rac-R"(bis(3-R-1-Op)), rac-R"(3-R-1-Op)(3-R-1-Cp), rac-R"(3-R-Op)$(ER^6{}_m)$, rac-R"(3-R-Op)$(E'R^7{}_n)$, rac-R"(bis(3-R-4-R'-1-Op)), rac-R"(bis(3-R-4-R'-1-Op)(3-R-4-R'-1-Cp), rac-R"(bis(3-R-1-Op)), rac-R"(3-R-Op)(3-R-1-Cp), rac-R"(3-R-Op)$(ER^6{}_m)$, and rac-A(3-R-Op)$(E'R^7{}_n)$,rac-R"(bis(3-R-4-R'-1-Op)), andrac-R"(bis(3-R-4-R'-1-Op)(3-R-4-R'-1-Cp); rac-R"(bis(3-R-1-o-Ind)), rac-R"(3-R-1-o-Ind)(3-R-1-Ind), rac-R"(3-R-1-o-Ind)$(ER^6{}_m)$, rac-R"(3-R-1-o-Ind)$(E'R^7{}_n)$; rac-R"(o-Flu)(3-R-Op), rac-R"(o-Flu)(3-R-1-Cp), rac-R"(o-Flu)$(ER^6{}_m)$, rac-R"(o-Flu)$(E'R^7{}_n)$, and the like where R", E, U and $R^{6-7}$ are as previously described, R and R' are as previously described for $R^{1-5}$, and where R is sterically larger than R'.

A few exemplified examples of metallocene ligands (R"YZ), that generate catalyst with varying amounts of syndiotactic selectivity would include, without limitation, R"(3,4-di-R-1-Op)(Op), R"(3,4-di-R-1-Op)(Cp), R"(3,4-di-R-1-Op)(3',4'-di-R'-1-Op), R"(3,4-di-R-1-Op)(3',4'-di-R'-1-Cp), R"(3,4-di-R-1-Cp)(3', 4'-di-R'-1-Op), R"(Op)(o-Flu), R"(Op)(Flu), R"(3,4-di-t-butyl-Op)(Flu), R"(3,4-di-t-butyl-Cp)(o-Flu), R"(3-o-Ind)(Op), R"(3-Ind)(Op), R"(3-o-Ind)

(Cp), and the like, where R" is as previously describe, and R and R' are as previously described for $R^{1-5}$, and where R is sterically larger than R'.

The unique and novel feature of the catalysts of the present invention are that the catalysts include at least one non-cyclopentadienyl six π electron ligand system which singly or in combination with a second such ligand, a Cp containing ligand, a nitrogen containing ligand, a phosphorus containing ligand, an oxygen containing ligand or a sulfur containing ligand can produce metallocene catalysts that are capable of producing all manners and types of polyolefin containing polymers including polymers where the polyolefins have varying to high degrees of stereoregularity.

Indeed, the present catalysts can be tailored using a number of strategies to control properties such as the relative stereospecificities of the polymer products produced, the molecular weight of the polymer products produced, and other significant polymer properties. The single carbon bridged metallocenes have been shown to be more stereospecific than the silicon bridged analogs for syndiotactic specific catalysts; the carbon bridged metallocenes are generally less stereospecific than the silicon bridged analogs for isospecific catalysts. It is thought that the larger the steric requirements are for the β-substituents, the more stereospecific the catalyst is. The difference in the steric requirements for the β-substituent can be used to optimize the orientation of the chain end which substituents at the α-position should result in increased polymer molecular weight.

The present invention is directed to both neutral metallocene and cationic metallocene catalysts and catalyst precursors as evidenced by the subscript 1 associated with the anion P having permissible values of 0 to 2, i.e., when l=0, the catalysts are neutral and when l=1 or 2 the catalysts are cationic.

The catalysts of the present invention can also be designed to produce polymers with very high tacticity indices depending on the desired tacticity. In order to produce the tactically specific catalysts and/or catalyst precursors of the present invention, the characteristics of the α and β substituents on the bridged ligands are important. Thus, the "steric requirement" or "steric size" of the α and β substituents are designed to control the steric characteristics of the catalyst/catalyst precursor such that the overall ligand system has $C_2$ or $C_s$ or pseudo-$C_2$ or pseudo-$C_s$ symmetry. This very specific arrangement of the α and β substituents allows control of the stereochemistry of each successive monomer addition.

The term CS or pseudo-$C_s$ symmetry means that the α and β substituents on each ligand are identical or similar, but for tactio selectivity it is necessary that the β-substituents on one ligand are sterically larger than the β-substituents on the other ligand. For example, the rac-isopropylidenebis(3-t-butyl-1-Op) ligand or the rac-isopropylidene(3-t-butyl-1-Op)(3'-t-butyl-1'-Cp) ligand would generate rac isospecific catalysts with $C_2$; the rac-isopropylidene(3-t-butyl-1-Op)(3'-t-butyl-4'-methyl-1'-Op) ligandortherac-isopropylidene(3-methyl-4-t-butyl-1-Op)(3-t-butyl-1-Cp) ligand would generate rac isoselective (less isospecific) catalysts with pseudo-$C_2$ symmetry (the meso isomer yields atactic polymer and can be separated from the rac catalyst by crystallization or other separation techniques well known in the art), while the isopropylidene(3,4-di-t-butyl-1-Op)(Op) ligand or the isopropylidene(3,4-di-t-butyl-1-Op)(Cp) ligand or isopropylidene(3,4-di-t-butyl-1-Cp)(Op) ligand or isopropylidene(3-t-butyl-1-Op)(Flu) ligand or related ligand would generate a syndiospecific catalyst with $C_s$ or pseudo-$C_s$ symmetry. Additionally, active isoselective catalysts can be prepared having one ligand characterized by bilateral or pseudo bilateral symmetry while the other ligand is not bilaterally or pseudo-bilaterally symmetric. Of course, for syndioselective catalysts, both ligands preferably are bilaterally or pseudo bilaterally symmetric.

A preferred class of Op ligands are those Op ligands where all five atomic centers are carbon atoms and where the 1, 3, and 4 positions of the Op ligand are substituted with bulky substituents such as iso-propyl groups, t-butyl groups, trialkylsilyl groups, and other similar bulky substituents. It is thought that such bulky groups stabilize the Op system.

It may also be possible to strategically arrange substituents with the proper steric properties on an appropriate carbon(s) of the open-fluorene ring(s) of, e.g., $R_2Si$ and Et bridged bisopen-fluorenyl complexes or mixed open-fluorene/fluorene complexes, which should serve as chain end conformational locks (preferably positioned in the mouth of the Flu ligand) and which could also confer solubility (ion pair separation for better catalyst activity and stereospecificity) and/or insolubility (for better control of polymer morphology); as desired. The bridged, substituted bisopen-fluorenyl or mixed open-fluorenyl/fluorenyl complexes are stereorigid, provide chain-end conformational locks, and are superior to those without such conformational locks.

Prior art has shown, for example, that a methyl substituent positioned at the α-Cp position on the C5 ring of bisindenyl catalysts increases the molecular weight of isotactic polypropylene produced with the $Et[Ind]_2ZrCl_2$ based catalyst. Similarly, a methyl substituent on the C6 ring of the indenyl ring system has reduced the stereospecificity; depending on the positional isomerism. These effects can be reasonably expected to carry over to the catalyst system of the present invention.

Also, the addition of methyl, t-Bu, OMe, Ph, etc. substituents to the o-Flu or Flu C6 ring and to the bridging group R" have had steric, solubility, and electronic influences on catalysts in syndiotactic and isotactic specific polymerizations. These effects are likewise expected to be carried over to metallocenes of the present invention and to their mixtures with other catalysts. Similarly the effects of substituting Al for B in the anions and the differences between carboranes and methylalumoxanes and other counter anions are reasonably expected to be carried over to the new catalyst systems described herein.

By making the sterically larger β-substituents different and/or the sterically smaller β-substituents different, the tactiospecific versions of the catalysts/catalyst precursors of the present invention can be designed to impart any degree of tacticity to the resulting polymers. Thus, if one β-substituent is t-butyl and another is ethyl, and the other two are hydrogens, the tactiospecificity of the catalyst system will be reduced relative to the one having two t-butyls and two hydrogens.

The concept of substituents with different steric requirements, size or bulk is well known in the art. However, to ensure that ordinary artisans understand its usage in the context of this invention, a non-exhaustive and illustrative list of the relative steric bulk of a variety of substituents can be found in Stoughtan and Adams article in J. Am. Chem. Soc., 54, 4426 (1932) and Yuan and Adams article in J. Am. Chem. Soc. 54, 4434 (1932).

Of course, cationic metallocene catalysts and catalyst precursors require the anion P to maintain net neutrality in the overall catalytic agent. The anion indicated by P in the general formula is preferentially a compatible non-coordinating or pseudo-non-coordinating anion that either does not coordinate with the metallocene cation or is only weakly coordinates to the metallocene cation to remain sufficiently labile so that it can be really displaced by a neutral Lewis base such as a monomer unit. Compatible non-coordinating or pseudo-non-coordinating anions are described as anions that stabilize the cationic metallocene catalyst systems, but do not transfer an anionic substituent or fragment to the cation to form a neutral metallocene and a neutral byproduct of the non-coordinately anion.

The useful size of the counterion P will also depend on the bulkiness or steric requirements of the substituent groups on the ligands of this invention. In addition to size, it is also thought that other characteristics are important for good anionic counterions. Such characteristics include stability and bonding. The anion must be sufficiently stable so that it cannot be rendered neutral by virtue of the metallocene cation extracting an electron. The bond strength with the cation is such that it does not interfere with monomer coordination and chain propagation.

A preferred procedure for producing cationic metallocene catalyst of the present invention (l=1 or 2) involves the reaction of an ion-pair in a non-coordinating solvent with a metallocene of the general formula where l=0, with one or more Lewis acids or P precursor agents. Thus, triphenylcarbenium tetrakis(pentafluorophenyl) boronate may be reacted with a neutral metallocene of the present invention in a solvent such as toluene to generate a cationic metallocene of the present invention. This preparation method was referenced in U.S. Pat. No. 5,225,508, incorporated by reference.

A preferred application of the present invention is in the polymerization of alpha olefins, specifically ethylene and propylene, into all manners of polymers including linear medium and high density polyethylene, atactic, isotactic, syndiotactic, hemi-isotactic polypropylenes or mixtures thereof. However, the invention may be employed in the preparation of hemi-isotactic, isotactic or syndiotactic polymers derived from other ethylenically unsaturated monomers. For example, syndiospecific, isospecific or hemi-isotactic specific polymers of 1-butene, 1-pentene, 1-hexene, styrene or the like.

Addition polymerizable monomers suitable for use in this invention are ethylenically unsaturated monomers including, without limitation, any organic molecule having a terminal vinyl group ($CH_2=CH-$) such as: $\alpha$-olefins including propylene, 1-butene, 1-pentene, 1-hexene, 4-methyl-1-pentene and the like; vinyl halides including vinyl fluoride, vinyl chloride, and the like; vinyl arenes including styrene, alkylated styrenes, halogenated styrenes, haloalkylated styrenes and the like; dienes such as 1,3-butadiene and isoprene (i.e., 1,2-addition). Polypropylene is probably of the greatest practical significance and the invention will be described in detail with reference to the production of polypropylene polymers of different tacticities. However, other polymers in which polymers having a desired tacticity are also of interest. These catalysts may also be useful in the polymerization of dienes to elastomers through the inclusion of 1,4-addition instead of 1,2-addition. Of course, these catalysts may also be useful in varying the relative amounts of 1,2-addition versus 1,4-addition polymers containing conjugated diene monomers. The term addition polymerizable monomer means all monomers that are polymerizable in an addition polymerization process with Ziegler, Ziegler-Natta, or Natta type transition metal polymerization catalysts.

The polymerization procedures disclosed in U.S. Pat. No. 4,892,851, may be also employed in carrying out the methods of the present invention and is incorporated herein by reference. Co-catalysts, usually organo-aluminum compounds such as trialkylaluminum, trialkyloxyaluminum, dialkylaluminum halides or alkylaluminum dihalides may be employed in the present invention. Especially suitable alkylaluminums are trimethylaluminum and triethylaluminum with the latter, commonly referred to as TEAL, being most preferred. Methylalumoxanes (MAO) are also usable in carrying out the methods of the present invention especially for neutral metallocene catalyst precursors. MAO may be used as a co-catalyst with metallocene catalysts in amounts well in excess of the stoichiometric equivalent.

Alumoxanes are polymeric aluminum compounds which can be represented by the general formulae $(R-Al-O)_n$ which is a cyclic compound and $R(R-Al-O-)_nAlR_2$, which is a linear compound. In the general formula R is a $C_1-C_5$ alkyl group such as, for example, methyl, ethyl, propyl, butyl and pentyl and n is an integer from 1 to about 20. Most preferably, R is methyl and n is about 4.

Generally, in the preparation of alumoxanes from, for example, aluminum trimethyl and water, a mixture of the linear and cyclic compounds is obtained. The alumoxane can be prepared in various ways. Preferably, they are prepared by contacting water with a solution of aluminum trialkyl, such as, for example, aluminum trimethyl, in a suitable organic solvent such as benzene or an aliphatic hydrocarbon. For example, the aluminum alkyl is treated with water in the form of a moist solvent. In an alternative method, the aluminum alkyl such as aluminum trimethyl can be desirably contacted with a hydrated salt such as hydrated copper sulfate. Preferably, the alumoxane is prepared in the presence of a hydrated copper sulfate. The method comprises treating a dilute solution of aluminum trimethyl in, for example, toluene, with copper sulfate represented by the general formula $CuSO_4.5H_2O$. The ratio of copper sulfate to aluminum trimethyl is desirably about 1 mole of copper sulfate for 4 to 5 moles of aluminum trimethyl. The reaction is evidenced by the evolution of methane.

The ratio of aluminum in the alumoxane to total metal in the metallocenes can be in the range of about 0.5:1 to about 10,000:1, and preferably about 5:1 to about 1000:1. The solvents used in the preparation of the catalyst system are inert hydrocarbons, in particular a hydrocarbon that is inert with respect to the catalyst system.

Such solvents are well known and include, for example, isobutane, butane, pentane, hexane, heptane, octane, cyclohexane, methylcyclohexane, toluene, xylene and the like. As a further control and refinement of polymer molecular weight, one can vary the concentration alumoxane. Higher concentrations of alumoxane in the catalyst system results in higher polymer product molecular weight.

The catalyst systems described herein are suitable for the polymerization of olefins in solution, slurry or gas phase polymerizations and over a wide range of temperatures and pressures. For example, such temperatures may be in the range of about $-60°$ C. to about 280° C. and especially in the range of about 50° C. to about 160° C. The pressures employed in the process of the present invention are those well known for, for example, in the range of about 1 to about 500 atmospheres and greater. In a solution phase polymerization, the alumoxane is preferably dissolved in a suitable solvent, typically in inert hydrocarbon solvent such as toluene, xylene, and the like in molar ratios of about $5 \times 10^{-3}$M. However greater or lesser amounts can be used. The solid catalysts in combination with an alumoxane can be usefully employed in slurry and gas phase olefin polymerizations.

After polymerization and deactivation of the catalyst, the product polymer can be recovered by processes well known in the art for removal of deactivated catalysts and solution. The solvents may be flashed off from the polymer solution and the polymer obtained extruded into water and cut into pellets or other suitable comminuted shapes. Pigments, antioxidants and other additives, as is known in the art, may be added to the polymer.

The polymer product obtained in accordance with this invention will have a weight average molecular weight in the range of about 1,400,000 to about 500 and preferably 500,000 to about 1000. The polydispersities (molecular weight distribution) expressed as Mw/Mn are typically from 1.5 to 4, but can be higher. The polymers can contain 1.0 chain end unsaturation per molecule. Broadened MW can be obtained by employing two or more of the metallocenes of this invention in combination with the alumoxane. The polymers produced by the process of this present invention are capable of being fabricated into a wide variety of articles, as is known for polymer products derived from addition polymerizable monomers.

While the applicant's invention is not to be restricted by theory, it is believed that neutral metallocenes form cationic complexes by reaction with the MAO in the manner as disclosed by Zambelli, A. et al., "Isotactic Polymerization of Propene: Homogenous Catalysts Based on Group 4 Metallocenes Without Methylaluminoxane", Macromolecules 1989, 22, pages 2186–2189.

The catalyst precursors used in the present invention may be prepared by procedures similar to those disclosed in U.S. Pat. No. 4,892,851, while the active cationic catalysts may be produced by simply converting the neutral metallocene into the cationic state following procedures such as those disclosed in European applications 277,003 and 277,004 or by reaction with triphenylcarbenium boronates. Similarly, alcohol —B(PhF)$_3$ complexes can be used as anionic precursors for forming the active cationic metallocenes of the present invention where the alcoholic proton reacts with an amine of an alkyl group on the coordinating metal atoms to generate a cationic metallocene and an alkoxide—B(PhF5)$_3$ anion. For additional information see, A. R. Siedle, W. M. Lammana, R. A. Newmark, J. St. Werrs, D. E. Richardson, M. Ryan, Makromol. Chem., Makromol. Symp. 66, 215 (1993).

The soluble, homogeneous catalysts of this invention can also be converted to supported heterogeneous catalysts by depositing the catalysts on supports including, without limitation, silica, alumina, magnesium dichloride, polystyrene beads, and like. The supported analogs of the present catalyst can improve the bulk density of the polymer as further described in Canadian Pat. No. 2,027,145, U.S. Pat. Nos. 4,935,474 and 4,530,914 and European Appln. Nos. 0,427,697 and 0,426,638, incorporated herein by reference.

The catalystd can also be chemically linked to the support by placing functional groups with ion pairs or Lewis acid centers or Lewis base centers on the ligands and/or supports. Supporting can also be achieved by using large (oligomeric or polymeric) insoluble anions as counter ions. Additionally, the catalysts of the present invention can be used to prepare low, moderate and high molecular weight polymers, low, moderate and high density polymers, elastomers, aspecific, isospecific, syndiospecific, hemi-isospecific, and/or aspecific polymers, not only of propylene, but for all α-olefins such as 1-butene, 1-pentene, 1-hexene, 4-methyl-1-pentene, $CH_2=CH(CH_2)_pSi(CH_3)_3$ where p is 1 to 4, and the like. Additionally, the catalysts of this invention can polymerize singly or in mixtures all addition polymerizable monomer including vinyl monomers and diene monomers.

One of ordinary skill should recognize that the ligands that can give rise to isoselective catalysts will give rise to a meso form which is asymmetric and a rac form that is selective to specific to isotactic polymers. The stereospecific rac catalysts can be separated from the meso form by crystallization. Perhaps we should also mention that it is well known from the Bercaw et al. work (Reference: J. Am. Chem Soc. 1992, 114, 7607 J. E. Bercaw and E. B. Coughlin.) in the prior art that rac-metallocenes free of the undesirable aspecific meso stereoisomers can be prepared by placing suitable bulky substituents such as $Si(Me)_3$ on the ligand atoms proximal to (α to) the bridgehead atom.

The catalysts of the present invention can obviously be used in conjunction with each other, all other metallocene catalysts, $TiCl_3$/DEAC, and or $TiCl_4/MgCl_2$/TEAL catalysts having internal electron donors such as diisobutylypthalate and external donors such as diphenyldimethoxysilane, methanol, etc. to produce polymers with mixed stereochemical compositions, distributions or tailored molecular weight distributions. Reactor blends of polymers with optimized physical, thermal, mechanical, and rheological properties can be tailored to produce the optimum mixture for specific applications requiring high melt strength, high clarity, high impact strength, and high rates of crystallization, simply by mixing catalyst species together in appropriate ratios.

The catalysts of the present invention clearly have the potential to influence the rate of termination by β-hydride elimination reactions. This, therefore, provides a novel ligand effect for controlling polymer molecular weights. These catalysts can be exploited to tailor molecular weights and hence molecular weight distributions with mixed species of the catalysts and any other class of catalysts. This would be advantageous in tailoring the polymer properties in HDPE, LLDPE, i-PP, s-PP, etc. Similarly the chain-end conformation locking substituent will influence the rate of reactivity of the new metallocenes with α-olefins such as propylene, butene and hexene. The new ligand effects on the catalyst reactivity ratios can be exploited to produce reactor blends with varying compositions, sequences, distributions and/or molecular weight distributions. Similarly, the catalysts can reasonably be expected to provide improved tailored grades of polypropylene and propylene-ethylene high impact copolymers as reactor blends or from reactors in series including fluidized and stirred gas phase polymerizations.

The catalysts of the present invention can also be used to generate copolymers of olefins and copolymers of olefins and dienes with varying degrees of tactiospecificity.

The generalized methods that follow describe the preparation of the catalyst and/or catalyst precursors and active catalysts. It is important that the catalyst complex be "pure" as low molecular weight, amorphous polymer can be produced by impure catalysts.

Generally, the preparation of the metallocene complex consists of forming and isolating the ligand system (bridged or unbridged) which are then aromatized or deprotonated to from delocalized electron systems or hetero anions and reacted with a metal halide, alkylide, or the like to form the complex.

The synthetic procedures are generally performed under an inert gas atmosphere using a glove box or Schlenk techniques. The synthesis process generally comprises the steps of 1) preparing the halogenated or alkylated metal compound, 2) preparing the ligand, 3) synthesizing the complex, and 4) purifying the complex.

The synthesis of Op's generally involves the reaction of a suitable 1,4-di-unsaturated compound directly with the metal species or with a strong base to render the delocalized six π electron anionic system and then reacting the anionic species with the metal species. In the case of bridged ligand systems of the present invention, the 1,4-di-unsaturated compounds are first reacted with a strong base such as lithium alkyl to produce the anion which can then be reacted with dialkyl dihalo silicon to produce silicon bridged ligand bis (Op) systems or with a fulvene to produce mixed Op-R"-Cp systems.

For hetero systems such as those containing one or more CN double bonds, CO double bonds, CP double bonds, or CS double bonds, the precursor reagents would be preferably reacted with strong basis such as an alkyl sodium, alkyl potassium, alkylaluminum, or similar reagents or with lithium metal, sodium metal or potassium metal to prevent addition to the hetero double bond.

Suitable 1,4-di-unsaturated compounds include 1,4-pentadiene and all substituted analogs thereof provided the C3 carbon has at least one hydrogen atom so that the system can be render anionic through deprotonation; 1-aryl-pent-2-enes, 1,1-diarylmethanes, α-γ or 1,3 diketones, dialdehydes, dithioketone, and dithioaldehydes (i.e., compounds represented by E'=CR—CHR—CR=E' where R is a hydrogen or any other substituent and E' is O or S), α-γ or 1,3 diimines or diphospines (i.e., compounds represented by RE=CR—CHR—CR=ER where R is a hydrogen or any other substituent and E is N or P); and analogs thereof where the C3 carbon atom is replaced by a N or P atom.

The synthesis of the β-substituted Cp ligands of the present invention can be accomplished by contacting an appropriately substituted fulvene with an appropriately substituted open-cyclopentadienyl containing anion under reaction conditions sufficient to produce a bridged structure having the requisite β-substituents on the Cp ring and the Op ligand to yield ligand systems with either $C_2$ or $C_s$ or pseudo $C_2$ or pseudo $C_s$ symmetry.

Fulvene is cyclopentadiene with an exo-cyclic methylene group at the 1 position of cyclopentadiene ring. The exo-cyclic methylene carbon is the 6 position of fulvene. Since this carbon can ultimately become the bridging group R" in formula (I), the preferred fulvenes for the preparation of the present catalysts are typically 6,6-disubstituted fulvenes so that the resulting bridging group is a tertiary carbon atom.

The fulvenes useful in preparing the ligands of the present invention have substituents in the 3 and 4 positions Q and are generally 6,6 disubstituted, while the other sites can be substituted or unsubstituted as shown below:

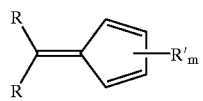

where $R'_m$ are as previously described and where the R groups and the exocyclic carbon (C6 in fulvene) is meant to be the precursor to the structural bridging group R".

As noted previously, a preferred mode of converting the neutral metallocenes to cationic metallocene catalyst useful in the present invention involves reaction of the neutral metallocenes with a triphenylcarbenium boronate. A preferred reactant is triphenylcarbenium tetrakis (pentafluorophenyl) boronate.

The catalysts of the present invention can also be made into efficient pre-polymerized catalysts by the methods disclosed in U.S. Pat. Nos. 3,893,989, 4,200,171, 4,287,328, 4,316,966 and 5,122,583 incorporated herein by reference. Essentially, the catalysts are used to polymerize monomer on a small scale to form a catalyst with a low molecular weight polymer surrounding and stabilizing the catalyst. The pre-polymerized catalysts can be prepared in the presence of co-catalysts such as the ones described previously and optionally in the presence of various electron donors.

The pre-polymerized catalysts can then be introduced into a reaction zone containing monomer. The resulting polymerization can show greatly improved catalytic efficiencies. The preferred methods for using pre-polymerized catalysts of the present invention are: (1) contacting a pre-polymerized catalyst of formula (I) with a co-catalyst and introducing the catalyst into a polymerization reaction zone containing monomer and (2) contacting a pre-polymerized catalyst of formula (I) with a co-catalyst and introducing the catalyst into a polymerization reaction zone containing monomer. Of course, the pre-polymerized catalysts of formula (I) can be introduced into the reaction zone in a stream either separately or in conjunction with separate streams containing the co-catalyst and/or electron donors.

Preferred pre-polymerized catalysts of the present invention have a weight ratio of polymer/catalyst of approximately 0.1–100 with ratios of less than 10 being particularly preferred. The syntheses are conveniently done at room temperature or lower in low boiling solvents which are readily evaporated in vacuo.

A general scheme of preparing the catalyst of formula (I) is outlined below for the synthesis of $Me_2Si(o-Flu)(Cp)$ $_2ZrCl_2$ as a catalyst precursor where Me represents a methyl group in following discussion and not the metal atom of the general formula.

Equal amounts of 1,1-diphenyl methane and Cp are reacted with one molar equivalence of an alkyl lithium such as methyllithium, n-butyllithium, or sec-butyllithium. To this 1 to 1 mixture of 1,1-diphenyl methyl anion and CpLi is added ½ equivalent of $Me_2SiCl_2$. The mixture makes three different ligand bis(Cp)$Me_2Si$, (Cp)(o-Flu)$Me_2Si$, and bis (o-Flu)$Me_2Si$. These ligands can be separated by standard separation techniques. The (Cp)(o-Flu)$Me_2Si$ or (O-Flu) $M_2S_i$ system can then be reaction with two molar equivalent of an alkyl lithium to produce the dianion which is then reacted with $ZrCl_4$ to form the desired metallocene.

The preparation for the non-aromatic containing Op ligands proceeds by reacting 1,5-di(trimethylsilyl)-1,4-pentadiene with an alkyl lithium reagant to which can be added 6,6-dimethylfulvene to form the isopropyldienyl(Cp) (3,4-di(trimethylsilyl)Op) ligand system. This ligand system can then be reacted with two equivalents of alkyl lithium to form the dianion which can be reacted with $ZrCl_4$.

Thus, while in accordance with the patent statutes, the best mode and preferred embodiments of the invention have been described, it is to be understood that the invention is not limited thereto, but rather is to be measured by the scope and spirit of the appended claims.

We claim:

1. A metallocene compound represented by the general formula

where:

Z' is a non-cyclopentyl, five centered, delocalized six π electron, pentahapto radical of the general formula (a):

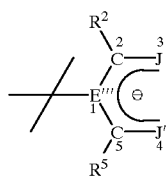

where:
- E''' is a carbon atom, a nitrogen atom, a silicon atom or a phosphorus atom; J and J' are the same or different, J is a $CR^3R^{3'}$ radical, a $SiR^3R^{3'}$ radical, an $NR^{3''}$ radical, a $PR^{3''}$ radical, an oxygen atom or a sulfur atom and J' is a $CR^4R^{4'}$ radical, a $SiR^4R^{4'}$ radical, an $NR^{4''}$ radical, a $PR^{4''}$ radical, an oxygen atom or a sulfur atom;
- $R^2$, $R^3$, $R^{3'}$, $R^{3''}$, $R^4$, $R^{4'}$, $R^{4''}$ and $R^5$ are the same or different and are a hydrogen atom, a linear or branched $C_1$–$C_{20}$ hydrocarbyl radical, a linear or branched $C_1$–$C_{20}$ halocarbyl radical, a $C_1$–$C_{20}$ hydrohalocarbyl radical, a linear or branched $C_1$–$C_{20}$ alkoxy radical, a $C_3$–$C_{12}$ cyclohydrocarbyl radical, a $C_3$–$C_{12}$ cyclohydrohalocarbyl radical, a silicon hydrocarbyl radical, a germanium hydrocarbyl radical, a phosphorous hydrocarbyl radical, a nitrogen hydrocarbyl radical, a boron hydrocarbyl radical, an aluminum hydrocarbyl radical, or a halogen atom or $R^2$ and $R^3$, $R^{3'}$ or $R^{3''}$ or $R^5$ and $R^4$, $R^{4'}$ or $R^{4''}$ or both $R^2$ and $R^3$, $R^{3'}$ or $R^{3''}$ and $R^5$ and $R^4$, $R^{4'}$ or $R^{4''}$ are joined together to form a $C_4$ to $C_6$ ring or a $C_6$ to $C_{20}$ ring system or where $R^3$, $R^{3'}$, or $R^{3''}$ and $R^4$, $R^{4'}$, or $R^{4''}$ are joined together to form a non-cyclopentyl ring;
- Z is the same or different non-cyclopentyl, five centered, delocalized six π electron, pentahapto radical as Z', or a Cp containing radical;
- R" is a structural bridge and is a $C_1$–$C_{20}$ alkenyl radical, a peralkylated $C_1$–$C_{20}$ alkenyl radical, a $C_3$–$C_{12}$ cyclohydrocarbyl radical, an aryl radical, a diaryl allyl radical, a silicon hydrocarbyl radical, a germanium hydrocarbyl radical, a phosphorous hydrocarbyl radical, a nitrogen hydrocarbyl radical, a boron hydrocarbyl radical, or an aluminum hydrocarbyl radical and where R" is bonded to position 1 of Z' and to position 1 of Z;
- M is a Group 3, 4, or 5 element from the Periodic Table of Elements, or Lu, La, Nd, Sm, or Gd;
- Q is a $C_1$–$C_{20}$ hydrocarbyl radical or a halogen atom;
- A is a counterion;
- k is an integer having a value from 1 to 3; and
- l is an integer having a value from 0 to 2.

2. The compound of claim 1, wherein either Z' or Z has at least one substituent β to its 1 position sterically larger than a hydrogen atom and where Z'R"Z has $C_2$ symmetry and the compound, in combination with a cocatalyst, generates polymers with varying degrees of isoselectivity from polymerizable vinyl monomers capable of generating polymers with varying degrees of tactioselectivity.

3. The compound of claim 1, wherein Z is a non-cyclopentyl, five centered, delocalized six π electron, pentahapto radical and Z' and Z are the same or different.

4. The compound of claim 1, wherein Z is a Cp containing radical.

5. The compound of claim 2, wherein the at least one β substituent is sterically larger than a methyl group.

6. The compound of claim 1, wherein either Z' or Z has at least one substituent β to its 1 position sterically larger than a hydrogen atom and where the compound, in combination with a cocatalyst, generates polymers with varying degrees of tactioselectivity from polymerizable vinyl monomers capable of generating polymers with varying degrees of tactioselectivity.

7. The compound of claim 1, wherein either Z' or Z has two substituents β to its 1 position sterically larger than a hydrogen atom and where Z'R"Z has $C_s$ symmetry and the compound, in combination with a cocatalyst, generates polymers with varying degrees of syndioselectivity from polymerizable vinyl monomers capable of generating polymers with varying degrees of tactioselectivity.

8. The compound of claim 7, wherein the β substituents are sterically larger than a methyl group.

9. The compound of claim 6, wherein the at least one β substituent is sterically larger than a methyl group.

10. A metallocene compound represented by the general formula:

$$Z'R"ZMQ_kA_l$$

where:
- Z' and Z are the same or different non-cyclopentyl, five centered, delocalized, six π electron, pentahapto radicals;
- R" is a structural bridge and is a $C_1$–$C_{20}$ alkenyl radical, a peralkylated $C_1$–$C_{20}$ alkenyl radical, a $C_3$–$C_{12}$ cyclohydrocarbyl radical, an aryl radical, a diaryl allyl radical, a silicon hydrocarbyl radical, a germanium hydrocarbyl radical, a phosphorous hydrocarbyl radical, a nitrogen hydrocarbyl radical, a boron hydrocarbyl radical, or an aluminum hydrocarbyl radical and where R" is bonded to position 1 of Z' and to position 1 of Z;
- M is a Group 3, 4, or 5 element from the Periodic Table of Elements, or Lu, La, Nd, Sm, or Gd;
- Q is a $C_1$–$C_{20}$ hydrocarbyl radical or a halogen atom;
- A is a counterion;
- k is an integer having a value from 1 to 3; and
- l is an integer having a value from 0 to 2.

11. The compound of claim 10, wherein Z' is a radical of the general formula (a):

where:
- E''' is a carbon atom, a nitrogen atom, a silicon atom or a phosphorus atom;
- J and J' are the same or different, J is a $CR^3R^{3'}$ radical, a $SiR^3R^{3'}$ radical, an $NR^{3''}$ radical, a $PR^{3''}$ radical, an oxygen atom or a sulfur atom and J' is a $CR^4R^{4'}$ radical, a $SiR^4R^{4'}$ radical, an $NR^{4''}$ radical, a $PR^{4''}$ radical, an oxygen atom or a sulfur atom;
- $R^2$, $R^3$, $R^{3'}$, $R^{3''}$, $R^4$, $R^{4'}$, $R^{4''}$, and $R^5$ are the same or different and are a hydrogen atom, a linear or branched $C_1$–$C_{20}$ hydrocarbyl radical, a linear or branched $C_1$–$C_{20}$ halocarbyl radical, a $C_1$–$C_{20}$ hydrohalocarbyl radical, a linear or branched $C_1$–$C_{20}$ alkoxy radical, a $C_3$–$C_{12}$ cyclohydrocarbyl radical, a $C_3$–$C_{12}$cyclohydrohalocarbyl radical, a silicon hydrocarbyl radical, a germanium hydrocarbyl radical, a phosphorous hydrocarbyl radical, a nitrogen hydrocarbyl radical, a boron hydrocarbyl radical, an aluminum hydrocarbyl radical, or a halogen atom or $R^2$ and $R^3$, $R^{3'}$ or $R^{3''}$ or $R^5$ and $R^4$, $R^{4'}$ or $R^{4''}$ or both $R^2$ and $R^3$, $R^{3'}$ or $R^{3''}$ and $R^5$ and $R^4$, $R^{4'}$ or $R^{4''}$ are joined together to form a $C_4$ to $C_6$ ring or a $C_6$ to $C_{20}$ ring system or where $R^3$, $R^{3'}$, or $R^{3''}$ and $R^4$, $R^{4'}$, or $R^{4''}$ are joined together to form a non-cyclopentyl ring.

12. The compound of claim 10, wherein either Z' or Z has at least one substituent β to its 1 position sterically larger than a hydrogen atom and where the compound, in combination with a cocatalyst, generates polymers with varying degrees of tactioselectivity from polymerizable vinyl monomers capable of generating polymers with varying degrees of tactioselectivity.

13. The compound of claim 10, wherein either Z' or Z has two substituents β to its 1 position sterically larger than a hydrogen atom and where Z'R"Z has $C_s$ symmetry and the compound, in combination with a cocatalyst, generates polymers with varying degrees of syndioselectivity from polymerizable vinyl monomers capable of generating polymers with varying degrees of tactioselectivity.

14. The compound of claim 10, wherein either Z' or Z has at least one substituent β to its 1 position sterically larger than a hydrogen atom and where Z'R"Z has $C_2$ symmetry and the compound, in combination with a cocatalyst, generates polymers with varying degrees of syndioselectivity from polymerizable vinyl monomers capable of generating polymers with varying degrees of tactioselectivity.

15. A metallocene compound represented by the general formula:

$$Z'R"ZMQ_kA_l$$

where:

Z' is a non-cyclopentyl, five centered, delocalized, six π electron, pentahapto radical;

Z is a Cp containing radical;

R" is a structural bridge and is a $C_1$–$C_{20}$ alkenyl radical, a peralkylated $C_1$–$C_{20}$ alkenyl radical, a $C_3$–$C_{12}$ cyclohydrocarbyl radical, an aryl radical, a diaryl allyl radical, a silicon hydrocarbyl radical, a germanium hydrocarbyl radical, a phosphorous hydrocarbyl radical, a nitrogen hydrocarbyl radical, a boron hydrocarbyl radical, or an aluminum hydrocarbyl radical and where R" is bonded to position 1 of Z' and to position 1 of Z;

M is a Group 3, 4, or 5 element from the Periodic Table of Elements, or Lu, La, Nd, Sm, or Gd;

Q is a $C_1$–$C_{20}$ hydrocarbyl radical or a halogen atom;

A is a counterion;

k is an integer having a value from 1 to 3; and l is an integer having a value from 0 to 2.

16. The compound of claim 15, wherein Z' is a radical of the general formula (a):

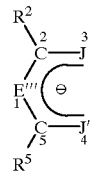

(a)

where:

E'" is a carbon atom, a nitrogen atom, a silicon atom or a phosphorus atom;

J and J' are the same or different, J is a $CR^3R^{3'}$ radical, a $SiR^3R^{3'}$ radical, an $NR^{3''}$ radical, a $PR^{3''}$ radical, an oxygen atom or a sulfur atom and J' is a $CR^4R^{4'}$ radical, a $SiR^4R^{4'}$ radical, an $NR^{4''}$ radical, a $PR^{4''}$ radical, an oxygen atom or a sulfur atom;

$R^2$, $R^3$, $R^{3'}$, $R^{3''}$, $R^4$, $R^{4'}$, $R^{4''}$, and $R^5$ are the same or different and are a hydrogen atom, a linear or branched $C_1$–$C_{20}$ hydrocarbyl radical, a linear or branched $C_1$–$C_{20}$ halocarbyl radical, a $C_1$–$C_{20}$ hydrohalocarbyl radical, a linear or branched $C_1$–$C_{20}$ alkoxy radical, a $C_3$–$C_{12}$ cyclohydrocarbyl radical, a $C_3$–$C_{12}$ cyclohydrohalocarbyl radical, a silicon hydrocarbyl radical, a germanium hydrocarbyl radical, a phosphorous hydrocarbyl radical, a nitrogen hydrocarbyl radical, a boron hydrocarbyl radical, an aluminum hydrocarbyl radical, or a halogen atom or $R^2$ and $R^3$, $R^{3'}$ or $R^{3''}$ or $R^5$ and $R^4$, $R^{4'}$ or $R^{4''}$ or both $R^2$ and $R^3$, $R^{3'}$ or $R^{3''}$ and $R^5$ and $R^4$, $R^{4'}$ or $R^{4''}$ are joined together to form a $C_4$ to $C_6$ ring or a $C_6$ to $C_{20}$ ring system or where $R^3$, $R^{3'}$, or $R^{3''}$ and $R^4$, $R^{4'}$, or $R^{4''}$ are joined together to form a non-cyclopentyl ring.

17. The compound of claim 15, wherein either Z' or Z has at least one substituent β to its 1 position sterically larger than a hydrogen atom and where the compound, in combination with a cocatalyst, generates polymers with varying degrees of tactioselectivity from polymerizable vinyl monomers capable of generating polymers with varying degrees of tactioselectivity.

18. The compound of claim 15, wherein either Z' or Z has two substituents β to its 1 position sterically larger than a hydrogen atom and where Z'R"Z has $C_s$ symmetry and the compound, in combination with a cocatalyst, generates polymers with varying degrees of syndioselectivity from polymerizable vinyl monomers capable of generating polymers with varying degrees of tactioselectivity.

19. The compound of claim 15, wherein either Z' or Z has at least one substituent β to its 1 position sterically larger than a hydrogen atom and where Z'R"Z has $C_2$ symmetry and the compound, in combination with a cocatalyst, generates polymers with varying degrees of syndioselectivity from polymerizable vinyl monomers capable of generating polymers with varying degrees of tactioselectivity.

* * * * *